US010087374B2

United States Patent
Mukherjee et al.

(10) Patent No.: US 10,087,374 B2
(45) Date of Patent: Oct. 2, 2018

(54) CONVERSION OF TRIACYLGLYCERIDES-CONTAINING OILS TO HYDROCARBONS

(71) Applicants: Chevron Lummus Global, LLC, Bloomfield, NJ (US); Applied Research Associates, Inc., Albuquerque, NM (US)

(72) Inventors: Ujjal K. Mukherjee, Montclair, NJ (US); Arun Arora, Bloomfield, NJ (US); Marvin I. Greene, Clifton, NJ (US); Edward Coppola, Bloomfield, NJ (US); Charles Red, Jr., Bloomfield, NJ (US); J. Steven Baxley, Bloomfield, NJ (US); Sanjay Nana, Bloomfield, NJ (US); Jeffrey Rine, Bloomfield, NJ (US)

(73) Assignees: Chevron Lummus Global, LLC, Bloomfield, NJ (US); Applied Research Associates, Inc., Albuquerque, NM (US)

( * ) Notice: Subject to any disclaimer, the term of this patent is extended or adjusted under 35 U.S.C. 154(b) by 150 days.

(21) Appl. No.: 14/885,135

(22) Filed: Oct. 16, 2015

(65) Prior Publication Data

US 2016/0040078 A1    Feb. 11, 2016

Related U.S. Application Data

(62) Division of application No. 13/711,111, filed on Dec. 11, 2012, now Pat. No. 9,162,938.

(51) Int. Cl.
*B01J 8/04*    (2006.01)
*C07C 1/22*    (2006.01)
(Continued)

(52) U.S. Cl.
CPC ............ *C10G 3/50* (2013.01); *B01J 19/0046* (2013.01); *C07C 1/22* (2013.01); *C10G 3/40* (2013.01);
(Continued)

(58) Field of Classification Search
CPC ... C10G 3/50; C10G 3/40; C10G 3/42; C10G 3/52; C10G 45/00; C10G 45/06;
(Continued)

(56) References Cited

U.S. PATENT DOCUMENTS 3,394,074 A * 7/1968 Buchmann ............. B01J 29/166
208/111.15
4,990,243 A    2/1991 Winslow et al.
(Continued)

FOREIGN PATENT DOCUMENTS

JP    2007-131595 A    5/2007
JP    2008-297452 A    12/2008
(Continued)

OTHER PUBLICATIONS

Notice of Reasons for Rejection dated Mar. 15, 2016 in corresponding Japanese application No. 2015-537030 (w/ translation) (5 pages).
(Continued)

*Primary Examiner* — Huy Tram Nguyen
(74) *Attorney, Agent, or Firm* — Osha Liang LLP (57) ABSTRACT

A process for converting triacylglycerides-containing oils into crude oil precursors and/or distillate hydrocarbon fuels is disclosed. The process may include: reacting a triacylglycerides-containing oil-water-hydrogen mixture at a temperature in the range from about 250° C. to about 525° C. and a pressure greater than about 75 bar to convert at least a portion of the triacylglycerides and recovering a reaction effluent comprising water and one or more of isoolefins, isoparaffins, cycloolefins, cycloparaffins, and aromatics;
(Continued)

hydrotreating the reaction effluent to form a hydrotreated effluent.

18 Claims, 2 Drawing Sheets

(51) Int. Cl.
| | |
|---|---|
| *C10G 45/00* | (2006.01) |
| *C10G 3/00* | (2006.01) |
| *B01J 19/00* | (2006.01) |
| *C10G 45/02* | (2006.01) |
| *C10G 45/32* | (2006.01) |
| *C10G 45/06* | (2006.01) |
| *C10G 45/08* | (2006.01) |
| *C10G 45/10* | (2006.01) |
| *C10G 47/16* | (2006.01) |
| *C10G 65/12* | (2006.01) |

(52) U.S. Cl.
CPC ............... *C10G 3/42* (2013.01); *C10G 3/52* (2013.01); *C10G 45/00* (2013.01); *C10G 45/02* (2013.01); *C10G 45/06* (2013.01); *C10G 45/08* (2013.01); *C10G 45/10* (2013.01); *C10G 45/32* (2013.01); *C10G 47/16* (2013.01); *C10G 65/12* (2013.01); *C10G 2300/1011* (2013.01); *C10G 2300/1014* (2013.01); *C10G 2300/1018* (2013.01); *C10G 2300/202* (2013.01); *C10G 2300/4081* (2013.01); *C10G 2400/02* (2013.01); *C10G 2400/04* (2013.01); *C10G 2400/08* (2013.01); *Y02P 30/20* (2015.11)

(58) Field of Classification Search
CPC ......... C10G 45/08; B01J 19/0046; B01J 8/04; C07C 1/22
USPC ........................................................ 422/630
See application file for complete search history.

(56) References Cited

U.S. PATENT DOCUMENTS

| | | | |
|---|---|---|---|
| 5,069,890 A | 12/1991 | Dai et al. | |
| 5,071,805 A | 12/1991 | Winslow et al. | |
| 5,073,530 A | 12/1991 | Bezman et al. | |
| 5,141,909 A | 8/1992 | Bezman | |
| 5,277,793 A | 1/1994 | Bezman et al. | |
| 5,366,615 A | 11/1994 | Bezman | |
| 5,409,617 A * | 4/1995 | Ross ..................... A62D 3/20 | |
| | | 210/762 | |
| 5,439,860 A | 8/1995 | Habib et al. | |
| 5,453,177 A * | 9/1995 | Goebel ................. C10G 49/22 | |
| | | 208/100 | |
| 5,593,570 A | 1/1997 | Habib et al. | |
| 5,817,901 A | 10/1998 | Trambouze et al. | |
| 5,959,167 A | 9/1999 | Shabtai et al. | |
| 5,986,022 A * | 11/1999 | Austin ................. B01J 19/1862 | |
| | | 526/65 | |
| 6,180,845 B1 | 1/2001 | Catallo et al. | |
| 6,514,897 B1 | 2/2003 | Moy et al. | |
| 6,573,417 B1 | 6/2003 | Rice | |
| 6,693,225 B2 | 2/2004 | Boyer et al. | |
| 6,860,986 B2 | 3/2005 | Timken et al. | |
| 6,872,685 B2 | 3/2005 | Timken | |
| 6,902,664 B2 | 6/2005 | Timken | |
| 7,232,935 B2 | 6/2007 | Jakkula et al. | |
| 7,459,597 B2 | 12/2008 | Koivusalmi et al. | |
| 7,473,811 B2 | 1/2009 | Eilos et al. | |
| 7,501,546 B2 | 3/2009 | Koivusalmi et al. | |
| 7,511,181 B2 | 3/2009 | Petri et al. | |
| 7,556,728 B2 | 7/2009 | Lehtonen et al. | |
| 7,691,159 B2 | 4/2010 | Li | |
| 7,754,931 B2 | 7/2010 | Monnier et al. | |
| 7,846,323 B2 | 12/2010 | Abhari et al. | |
| 7,850,841 B2 | 12/2010 | Koivusalmi et al. | |
| 7,880,049 B2 | 2/2011 | Dumesic et al. | |
| 7,915,460 B2 | 3/2011 | Kalnes et al. | |
| 7,928,079 B2 | 4/2011 | Hrabie et al. | |
| 7,960,596 B2 * | 6/2011 | Miller ................. C10G 50/00 | |
| | | 585/240 | |
| 7,964,761 B2 | 6/2011 | Zmierczak et al. | |
| 7,967,973 B2 | 6/2011 | Myllyoja et al. | |
| 7,982,075 B2 | 7/2011 | Marker et al. | |
| 7,982,076 B2 | 7/2011 | Marker et al. | |
| 7,982,077 B2 | 7/2011 | Kalnes et al. | |
| 7,982,078 B2 | 7/2011 | Brady et al. | |
| 7,982,079 B2 | 7/2011 | Marker et al. | |
| 7,989,671 B2 | 8/2011 | Strege et al. | |
| 7,998,339 B2 | 8/2011 | Myllyoja et al. | |
| 7,999,142 B2 | 8/2011 | Kalnes et al. | |
| 7,999,143 B2 | 8/2011 | Marker et al. | |
| 8,003,834 B2 | 8/2011 | Marker et al. | |
| 8,003,836 B2 | 8/2011 | Marker et al. | |
| 8,017,819 B2 | 9/2011 | Yao et al. | |
| 8,026,401 B2 | 9/2011 | Abhari et al. | |
| 8,039,682 B2 | 10/2011 | McCall et al. | |
| 8,053,615 B2 | 11/2011 | Cortright et al. | |
| 8,058,492 B2 | 11/2011 | Anumakonda et al. | |
| 8,066,867 B2 | 11/2011 | Dziabala et al. | |
| 8,067,653 B2 | 11/2011 | Bressler | |
| 8,067,657 B2 | 11/2011 | Duarte Santiago et al. | |
| 8,076,504 B2 | 12/2011 | Kubatova et al. | |
| 8,084,655 B2 | 12/2011 | Dindi et al. | |
| 8,142,527 B2 | 3/2012 | Herskowitz et al. | |
| 8,178,060 B2 | 5/2012 | Corradi et al. | |
| 8,217,210 B2 | 7/2012 | Agrawal et al. | |
| 8,221,706 B2 | 7/2012 | Petri et al. | |
| 8,231,804 B2 | 7/2012 | Abhari | |
| 8,231,847 B2 | 7/2012 | da Silva Ferreira Alves et al. | |
| 9,206,367 B2 | 12/2015 | Seames et al. | |
| 2004/0045870 A1 * | 3/2004 | Wrisberg ............... C10G 49/00 | |
| | | 208/59 | |
| 2007/0170091 A1 | 7/2007 | Monnier et al. | |
| 2007/0175795 A1 | 8/2007 | Yao et al. | |
| 2008/0071125 A1 * | 3/2008 | Li ......................... C10L 1/026 | |
| | | 585/361 | |
| 2008/0163543 A1 | 7/2008 | Abhari et al. | |
| 2009/0031617 A1 | 2/2009 | O'Rear | |
| 2009/0062578 A1 | 3/2009 | Koivusalmi et al. | |
| 2009/0077864 A1 | 3/2009 | Marker et al. | |
| 2009/0182106 A1 * | 7/2009 | Parola ................. B01J 19/1862 | |
| | | 526/161 | |
| 2009/0287029 A1 * | 11/2009 | Anumakonda .......... C10G 3/00 | |
| | | 585/16 | |
| 2009/0300970 A1 | 12/2009 | Perego et al. | |
| 2010/0000908 A1 | 1/2010 | Markkanen et al. | |
| 2010/0036183 A1 | 2/2010 | Gudde et al. | |
| 2010/0043278 A1 | 2/2010 | Brevoord et al. | |
| 2010/0113848 A1 | 5/2010 | Strege et al. | |
| 2010/0160698 A1 | 6/2010 | Perego et al. | |
| 2010/0163458 A1 | 7/2010 | Daudin et al. | |
| 2010/0237853 A1 | 9/2010 | Bose et al. | |
| 2010/0240942 A1 | 9/2010 | Daudin et al. | |
| 2010/0256428 A1 | 10/2010 | Marker et al. | |
| 2010/0317903 A1 | 12/2010 | Knuuttila | |
| 2011/0028773 A1 | 2/2011 | Subramaniam et al. | |
| 2011/0071327 A1 | 3/2011 | Abhari et al. | |
| 2011/0092746 A1 | 4/2011 | Dalloro et al. | |
| 2011/0105814 A1 | 5/2011 | Koivusalmi et al. | |
| 2011/0131867 A1 | 6/2011 | Kalnes et al. | |
| 2011/0155631 A1 | 6/2011 | Knuuttila et al. | |
| 2011/0160482 A1 | 6/2011 | Nagaki et al. | |
| 2011/0166396 A1 | 7/2011 | Egeberg et al. | |
| 2011/0209387 A1 | 9/2011 | Humphreys | |
| 2011/0230572 A1 | 9/2011 | Allison et al. | |
| 2011/0237838 A1 | 9/2011 | Zmierczak et al. | |
| 2011/0239532 A1 | 10/2011 | Baldiraghi et al. | |
| 2011/0289826 A1 | 12/2011 | Srinakruang | |
| 2011/0313219 A1 | 12/2011 | Fernando et al. | |
| 2011/0315596 A1 * | 12/2011 | Prentice ................. C10G 45/64 | |
| | | 208/59 | |

(56) References Cited

U.S. PATENT DOCUMENTS

| | | |
|---|---|---|
| 2012/0016167 A1 | 1/2012 | Hanks |
| 2012/0094879 A1 | 4/2012 | Roberts et al. |
| 2012/0095274 A1 | 4/2012 | Bao et al. |
| 2012/0142984 A1 | 6/2012 | Roberts et al. |
| 2012/0157734 A1 | 6/2012 | Strege et al. |

FOREIGN PATENT DOCUMENTS

| | | |
|---|---|---|
| WO | 2008020048 A2 | 2/2008 |
| WO | 2009015054 A1 | 1/2009 |
| WO | 2010011737 A2 | 1/2010 |
| WO | 2010053896 A2 | 5/2010 |

OTHER PUBLICATIONS

Notice of Reasons for Rejection dated Mar. 15, 2016 in corresponding Japanese application No. 2015-537029 (w/ translation) (7 pages).
Office Action issued in related U.S. Appl. No. 14/869,275 dated Apr. 7, 2017 (30 pages).
International Search Report and Written Opinion dated Mar. 27, 2014 in corresponding International Application No. PCT/US2013/073132 (14 pages).
Correspondence reporting an Official Letter and Search Report (w/translation) dated Jan. 19, 2015 in corresponding Taiwan application No. 102145419 (11 pages).
International Search Report issued in PCT/US2013/073121 dated Mar. 27, 2014 (2 pages).
Written Opinion of the International Searching Authority issued in in PCT/US2013/073121 dated Mar. 27, 2014 (7 pages).
Non-Final Office Action dated Dec. 3, 2015 in related U.S. Appl. No. 14/869,275 (25 pages).
Office Action issued in related U.S. Appl. No. 14/869,275 dated Aug. 22, 2016 (41 pages).
Extended European Search Report dated Jul. 12, 2016 in corresponding European application No. 13861979.6 (8 pages).
Office Action issued in related U.S. Appl. No. 14/651,611 dated Sep. 8, 2017 (34 pages).
Office Action issued in related U.S. Appl. No. 14/869,275 dated Jan. 26, 2018 (36 pages).
Office Action issued in corresponding EP Application No. 13861979.6 dated Mar. 2, 2018 (7 pages).

* cited by examiner

CONVERSION OF TRIACYLGLYCERIDES-CONTAINING OILS TO HYDROCARBONS

CROSS-REFERENCE TO RELATED APPLICATION

This application, pursuant to 35 U.S.C. § 120, claims benefit to U.S. patent application Ser. No. 13/711,111 filed Dec. 11, 2012. This application is incorporated herein by reference in their entirety.

FIELD OF THE DISCLOSURE

Embodiments disclosed herein relate generally to production of useful hydrocarbons, such as distillate fuels, from triacylglycerides-containing plant or animal fats-containing oils.

BACKGROUND

Hydrothermolysis of triacylglycerides-containing oils such as those derived from crops, animal fats or waste vegetable and animal-derived oils involves many types of chemical reactions. As one example, some prior art processes catalytically hydrotreat the triacylglyceride containing oils, converting the unsaturated aliphatic chains in the triacylglyceride containing oils to straight chain paraffins while simultaneously deoxygenating/decarboxylating the acid and glyceryl groups to form water, carbon dioxide and propane. Two downstream processes are then required to (a) skeletally isomerize the n-paraffins to isoparaffins to produce specification grade diesel fuels, and (b) hydrocracking the diesel range n-paraffins and isoparaffins to hydrocarbons to produce specification grade jet fuels.

U.S. Pat. No. 7,691,159, for example, discloses a hydrothermolysis process to convert triacylglycerides to smaller organic acids in the presence of hot compressed water at supercritical water conditions. During the process, the backbone of the triacylglycerides undergo rearrangement reactions.

SUMMARY OF THE DISCLOSURE

In one aspect, embodiments disclosed herein relate to a process for converting triacylglycerides-containing oils into crude oil precursors and/or distillate hydrocarbon fuels. The process may include: reacting a triacylglycerides-containing oil-water-hydrogen mixture at a temperature in the range from about 250° C. to about 525° C. and a pressure greater than about 75 bar to convert at least a portion of the triacylglycerides and recovering a reaction effluent comprising water and one or more of isoolefins, isoparaffins, cycloolefins, cycloparaffins, and aromatics; and hydrotreating the reaction effluent to form a hydrotreated effluent.

In another aspect, embodiments disclosed herein relate to a process for converting triacylglycerides-containing oils into crude oil precursors and/or distillate hydrocarbon fuels. The process may include: mixing a triacylglyceride-containing oil with water to form a triacylglycerides-water mixture; mixing hydrogen with the triacylglycerides-water mixture to form a mixed feed; reacting the mixed feed in a hydrothermolysis reaction zone under reaction conditions sufficient to convert at least a portion of the triacylglycerides via hydrothermolysis to produce hydrocarbon compounds comprising one or more of isoolefins, isoparaffins, cycloolefins, cycloparaffins, and aromatics; and recovering an effluent from the hydrothermolysis reaction zone; feeding effluent from the hydrothermolysis reaction zone, without any intermediate separations, to a catalytic hydrotreatment zone to hydrotreat the hydrothermolysis effluent; and recovering a hydrotreated effluent.

In another aspect, embodiments disclosed herein relate to a system for converting triacylglycerides-containing oils into crude oil precursors and/or distillate hydrocarbon fuels. The system may include: a mixing device for mixing a triacylglycerides-containing oil feed with water to form an oil-water mixture; a mixing device for mixing the oil-water mixture with hydrogen to form a feed mixture; a hydrothermolysis reactor for reacting the feed mixture at a temperature in the range of 250° C. to about 525° C. and a pressure greater than about 75 bar to produce a reaction effluent; a hydrotreater for hydrotreating the reaction effluent; and a separator for separating water and hydrogen from hydrocarbons in the hydrotreated effluent.

Other aspects and advantages will be apparent from the following description and the appended claims.

DETAILED DESCRIPTION

In one aspect, embodiments disclosed herein relate generally to production of useful hydrocarbons, such as paraffins, from triacylglycerides-containing oils, such as from renewable feedstocks. In another aspect, embodiments disclosed herein relate to processes and systems for converting triacylglycerides-containing oils into crude oil precursors and/or distillate hydrocarbon fuels.

Renewable feedstocks having triacylglycerides-containing oils useful in embodiments disclosed herein may include fatty acids, saturated triacylglycerides, and triacylglycerides having one or more olefinic bonds. For example, triacylglycerides-containing oils may include oils from at least one of camelina, carinata, jatropha, karanja, moringa, palm, castor, cotton, corn, linseed, peanut, soybean, sunflower, tung, babassu, and canola, or at least one triacylglycerides-containing oil from at least one of, shea butter, tall oil, tallow, waste vegetable oil, algal oil, and pongamia.

A mixture of the triacylglycerides-containing oil with water and hydrogen may be reacted at a temperature in the range from about 250° C. to about 525° C. and a pressure greater than about 75 bar to convert at least a portion of the triacylglycerides to a hydrocarbon or mixture of hydrocarbons comprising one or more of isoolefins, isoparaffins, cycloolefins, cycloparaffins, and aromatics. In some embodiments, the reaction conditions are such that the temperature and pressure are above the supercritical temperature and pressure of water. The resulting reaction effluent may then be further treated and separated to recover the hydrocarbon products.

To form the triacylglycerides-water-hydrogen mixture, a triacylglycerides-containing oil may be mixed with water and hydrogen in any order or with a mixture of water and hydrogen.

In some embodiments, to form the triacylglycerides-water-hydrogen mixture, triacylglycerides-containing oil is first mixed with water to form a triacylglyceride-water mixture. The resulting triacylglycerides-water mixture is then mixed with hydrogen to form the triacylglycerides-water-hydrogen mixture.

The triacylglycerides-water-hydrogen mixture may have a water to triacylglycerides mass ratio in the range from about 0.001:1 to about 1:1 in some embodiments; from about 0.01:1 to about 1:1 in other embodiments; and from about 0.1:1 to about 1:1 in yet other embodiments.

The triacylglycerides-water-hydrogen mixture may have a hydrogen to triacylglycerides mass ratio in the range from about 0.001:1 to about 0.5:1 in some embodiments; from about 0.01:1 to about 0.5:1 in other embodiments; and from about 0.1:1 to about 0.5:1 in yet other embodiments.

The reaction effluent may then be directly catalytically hydrotreated, without intermediate separations of water, unreacted hydrogen, or other light gas byproducts, to form additional distillate range hydrocarbons and/or to convert precursors in the reaction effluent to distillate range hydrocarbons. In some embodiments, the above-mentioned triacylglycerides-containing oils, following hydrothermolysis, may be co-processed in the hydrotreatment zone with other hydrocarbon feedstocks, such as atmospheric gas oil (AGO), vacuum gas oil (VGO), or other feeds derived from petroleum, shale oil, tar sands, coal-derived oils, organic waste oils, and the like.

Following hydrotreatment, the hydrotreatment effluent may then be processed to separate water, unreacted hydrogen, and light gases from the hydrotreatment effluent and to fractionate the hydrocarbons into one or more hydrocarbon fractions, such as those boiling in the range of naphtha, diesel, or jet. The water and hydrogen may then be recycled for admixture with the triacylglycerides-containing oil as described above.

The reaction of the triacylglycerides to produce hydrocarbons may be primarily a one or more hydrothermolysis reactions catalyzed by water and performed at a reaction temperature in the range from about 250° C. to about 525° C.; from about 350° C. to about 525° C. in some embodiments; and from about 425° C. to about 500° C. in other embodiments. Reaction conditions may also include a pressure of greater than 75 bar; greater than 150 bar in other embodiments; greater than 200 bar in other embodiments; between about 75 bar and about 300 bar in some embodiments; and between about 150 bar and about 250 bar in other embodiments. Conditions of temperature and/or pressure may be selected to be above the critical temperature and/or pressure of water. In all embodiments, the hydrothermolysis reactions may be performed in the absence of added catalysts, such as an inorganic heterogeneous catalyst.

Figure 1:
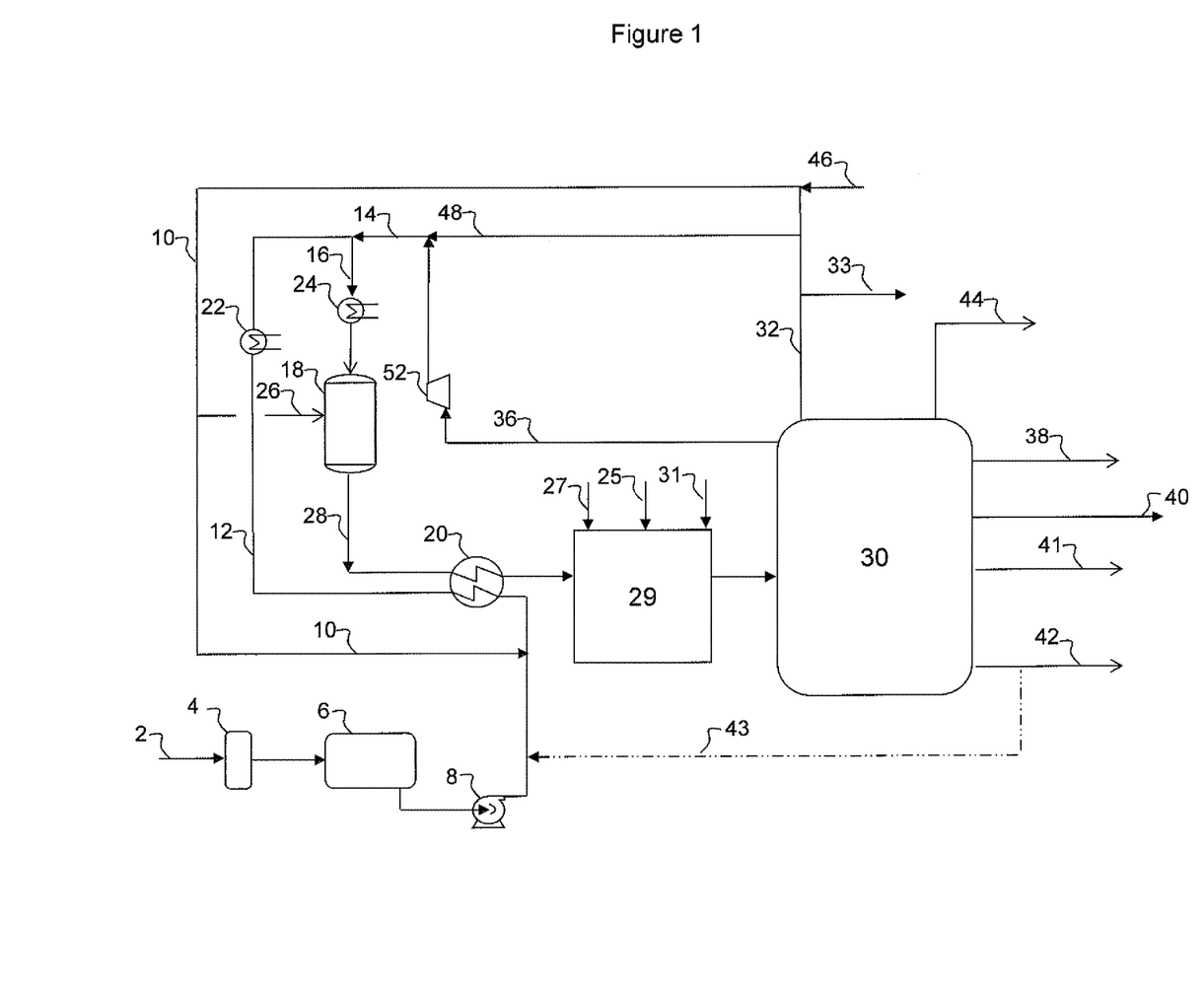
FIG. 1 is a simplified process flow diagram of a process according to embodiments herein.

Referring now to FIG. 1, a simplified process flow diagram of a process for converting triacylglycerides-containing oils into crude oil precursors and/or distillate hydrocarbon fuels according to embodiments herein is illustrated. A triacylglycerides-containing oil may be provided to the system via flow line 2, filtered if necessary in a filter 4, and stored in feed tank 6. The triacylglycerides-containing oil may then be fed via pump 8 and mixed with water fed via flow line 10. Mixing of the triacylglycerides-containing oil with water may be performed in a mixing device, such as a mixing tee, an agitated vessel, an in-line mixer or other mixing devices as known to those of skill in the art.

The triacylglycerides-water mixture 12 may then be combined with hydrogen fed via flow line 14 to form a triacylglycerides-water-hydrogen mixture 16. Mixture 16 may then be fed to hydrothermolysis reactor 18 and maintained at reaction conditions for a time sufficient to convert at least a portion of the triacylglycerides to distillate hydrocarbons or precursors thereof. Reaction conditions may include a temperature in the range from about 250° C. to about 525° C. and a pressure of at least 75 bar. The residence time required in reactor 18 to convert the triacylglycerides may vary depending upon the reaction conditions as well as the specific triacylglycerides-containing oil used. In some embodiments, residence times in reactor 18 may be in the range from about 3 to about 6 minutes. To elevate the temperature of the feed to reaction conditions, heat may be supplied to the feed via one or more of a feed-effluent exchanger 20, an indirect heat exchanger 22 to heat the triacylglycerides-water mixture 12, and an indirect heat exchanger 24 to heat the triacylglycerides-water-hydrogen mixture 16, among other options. The hydrothermolysis reaction can also include some exothermic reactions, which may supply additional heat to maintain the required reaction temperature conditions and to reduce external heat input requirements. In some embodiments, one or more water feed lines 26 may be provided to control the exotherm and the temperature or temperature profile in hydrothermolysis reactor 18.

Following reaction of the triacylglycerides in hydrothermolysis reactor 18, the reaction effluent 28 may be used to preheat the feed in feed-effluent exchanger 20, and further processed to recover the distillate hydrocarbons. Hydrothermolysis effluent 28 may then be fed, without separation of the water from the hydrothermolysis effluent, to a hydrotreatment system 29 to further treat the effluent. Hydrotreatment system 29 may include one or more reactors (hydrotreaters) (not shown) containing a hydroconversion catalyst to convert at least a portion of the hydrothermolysis effluent to distillate hydrocarbons. Additional hydrogen, if necessary, may be added to hydrotreatment system 29 via flow line 27. Further, as noted above, additional hydrocarbon feedstocks may be co-processed with hydrothermolysis effluent 28, and may be fed to hydrotreatment system 29 via flow line 25. Non-renewable hydrocarbon feedstocks, for example, may include one or more of petroleum distillates; shale oil distillates; tar sands-derived distillates; coal gasification byproduct oils; and coal pyrolysis oils, among others. If necessary, some sulfur-containing compound such as, for example, dimethyl disulfide dissolved in a suitable hydrocarbon solvent, may be fed to hydrotreatment system 29 via flow line 31 in order to maintain the catalysts in their most active states.

The hydrotreatment effluent may then be fed to effluent treatment system 30 for separation and recovery of reaction products. For example, effluent treatment system 30 may separate water 32 and hydrogen 36 from the hydrocarbons. The resulting hydrocarbons may also be fractionated into two or more fractions, which, as illustrated, may include distillate hydrocarbons boiling in the range of naphtha 38, diesel 41, or jet 40, and vacuum gas oil (VGO) 42. Some offgas 44 may also be produced.

A portion of water fraction 32 may be purged via flow line 33, if and as necessary, to avoid buildup of organic acids or other reaction byproducts. The water fraction 32 and the hydrogen fraction 36 may then be recycled and combined, as necessary, with makeup water 46 and makeup hydrogen 48, respectively, for mixture with the triacylglycerides-containing oil as described above. Compressor 52 may be used to pressurize the hydrogen recycle. In some embodiments, a heavy hydrocarbon recycle fraction 43 may also be recovered, and may be recycled to the hydrothermolysis reactor system 18, hydrotreatment system 29, or a combination thereof.

Figure 2:
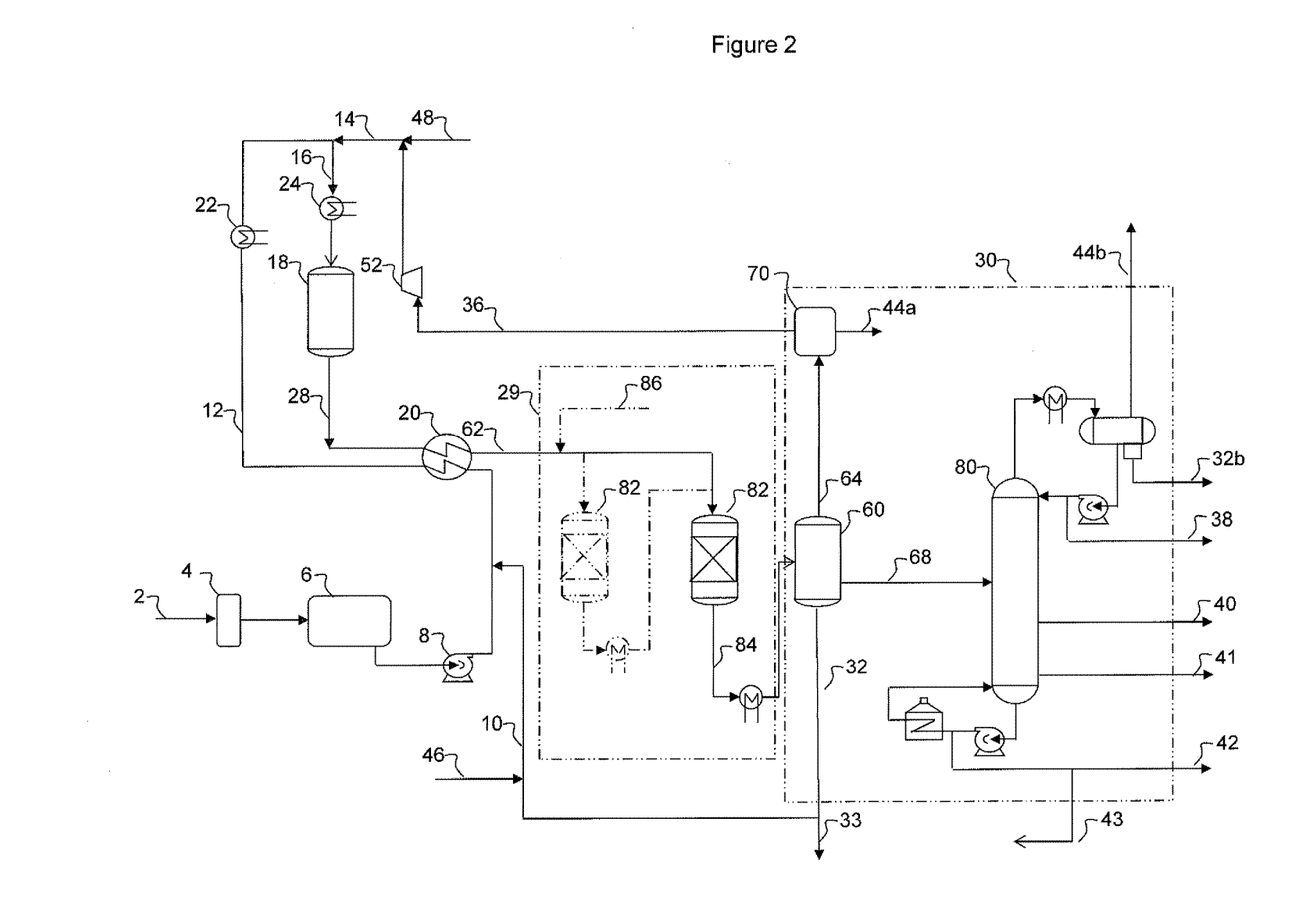
FIG. 2 is a simplified process flow diagram of a process according to embodiments herein.

Referring now to FIG. 2, a simplified process flow diagram of a process for converting triacylglycerides-containing oils into crude oil precursors and/or distillate hydrocarbon fuels according to embodiments herein is illustrated, where like numerals represent like parts. In this embodiment hydrotreatment system 29 may include a hydrotreater 82 for further converting the crude oil precursors and/or distillate hydrocarbon fuels in hydrothermolysis effluent 28. The hydrothermolysis effluent 28, 62, including hydrogen and water, may be fed to a hydrotreater 82 and contacted with a suitable catalyst to produce desired end products, such as jet, naphtha, and diesel boiling range hydrocarbons. If necessary, additional hydrogen may be added to the hydrothermolysis effluent prior to hydrotreatment via flow line 86.

Following hydrotreatment, the hydrotreated effluent 84 may then be fed to effluent treatment system 30. As illustrated in FIG. 2, effluent treatment system 30 may include a drum 60 for separation of the gaseous components from the liquid components in the cooled effluent 62. The gaseous components, including hydrogen and possibly some light reaction byproducts, may be recovered from drum 60 via flow line 64. Liquid components may settle in the bottom of drum 60, resulting in formation of a two-phase system, where the water may be recovered via flow line 32 and the hydrocarbons may be recovered via flow line 68. The water fraction 32 recovered from drum 60 may then be purged and/or recycled as described above.

Following separations in drum 60, the gaseous products in flow line 64 may be separated via a gas separation device 70 to result in a recycle hydrogen fraction 36 and an off-gas fraction 44a, as described above. The liquid hydrocarbon products may then be fed to a fractionator 80 for separation of the hydrocarbons into one or more boiling range fractions including naphtha 38, jet 40, diesel 41, and vacuum gas oil (VGO) 42. An additional off-gas fraction 44b and water fraction 32b may also result from separations in fractionator 80.

To produce additional distillate range fuels, such as where C20+ hydrocarbons are produced in hydrothermolysis reactor 18, some of the VGO fraction 42 may be recycled back to the hydrothermolysis reactor 18 for additional processing, such as via flow line 43.

As described with respect to the embodiments of FIGS. 1 and 2, there is no separation of the hydrothermolysis effluent before hydrotreatment. The hydrothermolysis step and feed of the entire hydrothermolysis effluent stream is performed in a close-coupled system, where no intermediate separations are performed. One skilled in the art may anticipate that such a close-coupled system would not be technically feasible, expecting the active metals in the supported catalysts to be solubilized or decrepitated; However, it has been found that catalyst activity may be maintained, over several hundred hours of pilot plant operations, even in the presence of high water concentrations and high organic acid concentrations (i.e., a much higher level of oxygenates than are normally encountered with typical petroleum feedstocks). Injection of water, hydrocarbons, free fatty acids, alcohols, and unconverted triacylglycerides directly to a hydrotreatment zone may thus provide for a significant reduction in unit operations and processing steps required to produce the desired distillate fuels.

Catalysts useful in hydrotreater 82 may include catalysts that may be used for the hydrotreating or hydrocracking of a hydrocarbon feedstock. In some embodiments, the hydrotreating catalyst may effectively hydrodeoxygenate and/or decarboxylate the oxygen bonds contained in the hydrotreater feed reduce or eliminate the organic acid concentration in effluent 28. In some embodiments, greater than 99%, 99.9%, or 99.99% of the organic acids may be converted over the hydrotreatment catalyst.

Hydrotreating catalysts that may be useful include catalysts selected from those elements known to provide catalytic hydrogenation activity. At least one metal component selected from Group 8-10 elements and/or from Group 6 elements is generally chosen. Group 6 elements may include chromium, molybdenum and tungsten. Group 8-10 elements may include iron, cobalt, nickel, ruthenium, rhodium, palladium, osmium, iridium and platinum. The amount(s) of hydrogenation component(s) in the catalyst suitably range from about 0.5% to about 10% by weight of Group 8-10 metal component(s) and from about 5% to about 25% by weight of Group 6 metal component(s), calculated as metal oxide(s) per 100 parts by weight of total catalyst, where the percentages by weight are based on the weight of the catalyst before sulfiding. The hydrogenation components in the catalyst may be in the oxidic and/or the sulphidic form. If a combination of at least a Group 6 and a Group 8 metal component is present as (mixed) oxides, it will be subjected to a sulfiding treatment prior to proper use in hydrocracking. In some embodiments, the catalyst comprises one or more components of nickel and/or cobalt and one or more components of molybdenum and/or tungsten or one or more components of platinum and/or palladium. Catalysts containing nickel and molybdenum, nickel and tungsten, platinum and/or palladium are useful.

In some embodiments, hydrotreater 82 may include two or more beds or layers of catalyst, such as a first layer including a hydrocracking catalyst and a second layer including a hydrotreating catalyst.

In some embodiments, the layered catalyst system may include a lower catalyst layer that includes a bed of a hydrocracking catalyst suitable for hydrocracking any vacuum gas oil (VGO) range hydrothermolysis products or added feeds to diesel range or lighter hydrocarbons. The hydrocracking catalysts used may also be selected to minimize or reduce dearomatization of the alkylaromatic formed in the hydrothermolysis reactor. VGO cracking catalysts that may be used according to embodiments herein include one or more noble metals supported on low acidity zeolites wherein the zeolite acidity is widely distributed throughout each catalyst particle. For example, one or more catalysts as described in U.S. Pat. Nos. 4,990,243, 5,069,890, 5,071,805, 5,073,530, 5,141,909, 5,277,793, 5,366,615, 5,439,860, 5,593,570 6,860,986, 6,902,664, and 6,872,685 may be used in embodiments herein, each of which are incorporated herein by reference with respect to the hydrocracking catalysts described therein. In some embodiments, the inclusion of the VGO hydrocracking may result in extinctive hydrocracking of the heavy hydrocarbons, such that the only net hydrocarbon products include diesel range and lighter hydrocarbons.

One skilled in the art will recognize that the various catalyst layers may not be made up of only a single catalyst, but may be composed of an intermixture of different catalysts to achieve the optimal level of metals or carbon residue removal and deoxygenation for that layer. Although some olefinic bond hydrogenation will occur in the lower portion of the zone, the removal of oxygen, nitrogen, and sulfur may take place primarily in the upper layer or layers. Obviously additional metals removal also will take place. The specific catalyst or catalyst mixture selected for each layer, the number of layers in the zone, the proportional volume in the bed of each layer, and the specific hydrotreating conditions selected will depend on the feedstock being processed by the unit, the desired product to be recovered, as well as commercial considerations such as cost of the catalyst. All of these parameters are within the skill of a person engaged in the petroleum processing industry and should not need further elaboration here.

While the above-described systems are described with respect to a single hydrothermolysis reactor 18 and a single hydrotreater 82, the reaction zones may include two or more reactors arranged in series or in parallel. Likewise, back-up compressors, filters, pumps, and the like may also be used. Further, compressors may be single stage or multi-stage compressors, which in some embodiments may be used to compress a single gas stream in sequential stages or may be used to compress separate gas streams, depending on plant layout.

As described above with respect to FIG. 2, fractionator 80 may be used to recover various hydrocarbon fractions. Where hydrotreater 82 includes a bed or layer of hydrocracking catalyst, production of heavy hydrocarbons may be reduced or eliminated. In such embodiments, fractionator 80 may be used to recover a diesel fraction as the bottoms from the column, and recycle of heavy hydrocarbons, such as VGO, may be unnecessary. When produced, the VGO may be recycled, as described above, or may be recovered as a low sulfur fuel oil product.

As described above, processes disclosed herein may be performed in a system or apparatus for converting triacylglycerides-containing oils into crude oil precursors and/or distillate hydrocarbon fuels. The system may include one or more mixing devices for mixing a triacylglycerides-containing oil feed with water and hydrogen. For example, the system may include a first mixing device for mixing a triacylglycerides-containing oil feed with water to form an oil-water mixture, and a second mixing device for mixing the oil-water mixture with hydrogen to form a feed mixture.

The resulting mixture may then be fed via a flow conduit to a hydrothermolysis reactor for reacting the feed mixture at a temperature in the range of 250° C. to about 525° C. and a pressure greater than about 75 bar to produce a reaction effluent. The hydrothermolysis reactor may include, for example, one or more tubular conduits within a furnace configured to maintain a temperature of the hydrothermolysis reactor effluent proximate an outlet of the hydrothermolysis reactor at reaction conditions, such as a temperature in the range from about 400° C. to about 525° C., or at a temperature and pressure greater than the critical temperature and pressure of water. The furnace may be, for example, an electrically heated furnace, or a furnace fired with a fuel gas, such as a natural gas, synthesis gas, or light hydrocarbon gases, including those produced in and recovered from the hydrothermolysis reactor. Reaction conditions may be achieved by use of one or more pumps, compressors, and heat exchangers. A separator may then be used for separating water and hydrogen from hydrocarbons in the reaction effluent.

The system may also include a compressor for compressing hydrogen recovered from the separator, as well as one or more fluid conduits for recycling the compressed hydrogen and/or the recovered water to the mixing device for mixing hydrogen or the mixing device for mixing water. The system also includes a hydrotreater to hydrotreat at least a portion of the hydrothermolysis reaction effluent.

The system may also include a fractionator for fractionating hydrocarbons in the hydrotreater effluent to form one or more hydrocarbon fractions boiling in the naphtha, jet or diesel range.

To control reaction temperatures and exotherms in the hydrothermolysis reactor, the system may include one or more fluid conduits for injecting water into the hydrothermolysis reactor.

As described above, embodiments disclosed herein provide processes for the conversion of renewable feedstocks to infrastructure-compatible distillate fuels. For example, in some embodiments, the jet fraction recovered may have a total acid number of less than 0.015 expressed as mg KOH per gram; less than 0.010 in other embodiments. The jet may have an olefins content of less than about 5 vol % and an aromatics content of less than about 25 vol % in some embodiments. These properties, among others, may allow the jet and/or the diesel fractions produced in embodiments herein to be used directly as a fuel without blending. In some embodiments, the whole hydrocarbon liquid product recovered from the hydrotreatment reaction zone may be used to produce distillate fuels meeting military, ASTM, EN, ISO, or equivalent fuel specifications.

The process may be carried out in an economically feasible method at a commercial scale. Embodiments herein may maximize the thermal efficiency of the triacylglycerides-containing oil conversion in an economically attractive manner without being hampered by operability problems associated with catalyst fouling. During the hydrothermolysis process, water, such as about 5% of the feed water, may be consumed in the hydrolysis reaction. In the hydrotreater, much of the glycerin byproduct produced may be further hydrogenated and converted to propane. Hydrogen is consumed during the hydrotreating step, and the average specific gravity of the product may be reduced, such as from approximately 0.91 to about 0.8. Decarboxylation reactions form COx and that carbon loss may result in a reduced mass yield of liquid products, and an equivalent lower volumetric yield. The actual crude yield may be in the range from about 75% to about 90%, such as in the range from about 80% to 84%, depending on how the hydrothermolysis process is executed.

Naphtha, jet, and diesel fuels may be produced by processes disclosed herein. A higher boiling gas oil material may also be produced, and may contain high-quality, high hydrogen content paraffins in the C17 to C24 boiling range. These heavier hydrocarbons may be recycled to the hydrothermolysis reactor for further treatment and production of naphtha, jet, and diesel range products. Fuel gases (off gases) may also be produced, which may be used in some embodiments for process heat, hydrogen production, or recovered as individual products (LPG, ethylene, propylene, n-butane, iso-butane, etc.).

Fuels produced by embodiments herein may: contain cycloparaffins and aromatics; exhibit high density; exhibit high energy density; exhibit good low-temperature properties (freezing point, cloud point, pour point, and viscosity); exhibit natural lubricity; exhibit a wide range of hydrocarbon types and molecular weights similar to petroleum; and/or have good thermal stability. These fuels may thus be true "drop in" analogs of their petroleum counterparts and do not require blending to meet current petroleum specifications.

Coupling of the hydrothermolysis reaction and hydrotreating is unique and may result in many process and economic benefits. For example, benefits may include: elimination of a hydrothermolysis product cool down and separation of gas, oil, and water components; elimination of acid water production and treatment; elimination of additional liquid pumping, gas compression, and heat exchange operations for the hydrotreater feed; reduced heat loss; and/or reduced power consumption.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A system for converting triacylglycerides-containing oils into crude oil precursors and/or distillate hydrocarbon fuels, the system comprising:
   a mixing device for mixing a triacylglycerides-containing oil feed with water to form an oil-water mixture;
   a mixing device for mixing the oil-water mixture with hydrogen to form a feed mixture;
   a hydrothermolysis reactor for reacting the feed mixture at a temperature in the range of 250° C. to about 525° C. and a pressure greater than about 75 bar to produce a reaction effluent;
   a hydrotreater for hydrotreating the reaction effluent, the system is configured to feed the reaction effluent to the hydrotreater without intermediate separation of water;
   a separator for separating water and hydrogen from hydrocarbons in the hydrotreated effluent.

2. The system of claim 1, further comprising one or more fluid conduits for recycling the hydrogen to the mixing device for mixing hydrogen.

3. The system of claim 1, further comprising a feed-effluent exchanger configured to preheat with feed mixture via indirect heat exchange with the reaction effluent.

4. The system of claim 1, wherein the hydrotreater comprises at least two catalyst beds, and wherein:
   a first catalyst bed comprises a catalyst having hydrogenation activity;
   a second catalyst bed comprises a catalyst having hydrocracking activity.

5. The system of claim 1, wherein the catalyst bed proximate an inlet of the hydrotreater comprises a catalyst useful for at least one of:
   decarboxylation;
   hydrodeoxygenation of unsaturated free fatty acids to produce C5-C24 paraffins;
   saturation of mono-, di- and tri-olefins contained in the alkyl backbone of the free fatty acids;
   hydrodenitrogenation of trace organic nitrogen compounds; and
   catalyst tolerance for water coming in with the hydrocarbonaceous feed.

6. The system of claim 5, wherein the catalysts having hydrocracking activity are comprised of one or more noble metals supported on low acidity zeolites wherein the zeolite acidity is widely distributed throughout each catalyst particle.

7. The system of claim 1, further comprising one or more fluid conduits for co-processing a non-renewable hydrocarbon feedstock with the reaction effluent in the hydrotreater.

8. The system of claim 1, wherein the hydrothermolysis reactor comprises one or more tubular conduits within a furnace configured to maintain a temperature of the hydrothermolysis reactor effluent proximate an outlet of the hydrothermolysis reactor at a temperature in the range from about 400° C. to about 525° C.

9. A system for converting triacylglycerides-containing oils into crude oil precursors and/or distillate hydrocarbon fuels, the system comprising:
   one or more mixing devices for mixing a triacylglycerides-containing oil feed with water, and hydrogen, together or separately, to form a feed mixture;
   a hydrothermolysis reactor for reacting the feed mixture to produce a reaction effluent;
   one or more fluid conduits configured to inject water into the hydrothermolysis reactor to maintain a temperature or temperature profile within the hydrothermolysis reactor;
   a hydrotreater for hydrotreating the reaction effluent, wherein no separator is located intermediate the hydrotheimolysis reactor and the hydrotreater;
   a separator for separating water and hydrogen from hydrocarbons in the hydrotreated effluent.

10. The system of claim 9, further comprising a fractionator for fractionating hydrocarbons in the hydrotreated effluent to form one or more hydrocarbon fractions boiling in the naphtha, jet or diesel range.

11. The system of claim 9, wherein the hydrotreater comprises at least two catalyst beds, and wherein:
    a first catalyst bed comprises a catalyst having hydrogenation activity;
    a second catalyst bed comprises a catalyst having hydrocracking activity.

12. The system of claim 9, wherein the catalyst bed proximate an inlet of the hydrotreater comprises a catalyst useful for at least one of:
    decarboxylation;
    hydrodeoxygenation of unsaturated free fatty acids to produce C5-C24 paraffins;
    saturation of mono-, di- and tri-olefins contained in the alkyl backbone of the free fatty acids;
    hydrodenitrogenation of trace organic nitrogen compounds; and
    catalyst tolerance for water coming in with the hydrocarbonaceous feed.

13. The system of claim 12, wherein the catalysts having hydrocracking activity are comprised of one or more noble metals supported on low acidity zeolites wherein the zeolite acidity is widely distributed throughout each catalyst particle.

14. The system of claim 9, further comprising a feed preheater configured to elevate the temperature of the feed mixture prior to the hydrothermolysis reactor.

15. A system for converting triacylglycerides-containing oils into crude oil precursors and/or distillate hydrocarbon fuels, the system comprising:
    a mixing device for mixing a triacylglycerides-containing oil feed with water and hydrogen to form a feed mixture;
    a hydrothermolysis reactor for reacting the feed mixture at a temperature in the range of 250° C. to about 525° C. and a pressure greater than about 75 bar to produce a reaction effluent comprising water, hydrogen, and hydrocarbons, wherein the hydrothermolysis reactor is configured to conduct the reacting in the absence of an added inorganic heterogeneous catalyst;
    a hydrotreater for hydrotreating the reaction effluent comprising water, hydrogen, and hydrocarbons, wherein no separator is located intermediate the hydrothermolysis reactor and the hydrotreater: and
    a separator for separating water and hydrogen from hydrocarbons in the hydrotreated effluent.

16. The system of claim 15, further comprising a feed-effluent exchanger configured to preheat with feed mixture via indirect heat exchange with the reaction effluent.

17. The system of claim 15, wherein the hydrotreater comprises at least two catalyst beds, and wherein:
- a first catalyst bed comprises a catalyst having hydrogenation activity;
- a second catalyst bed comprises a catalyst having hydrocracking activity.

18. The system of claim 15, wherein the separator further comprises:
- a drum configured to separate hydrogen and light byproducts from water and hydrocarbons, and to produce a gas stream, a water stream, and a hydrocarbon stream;
- a fractionator configured to separate the hydrocarbons into one or more fractions boiling in the naphtha, jet or diesel range;
- a gas separator configured to separate hydrogen from light byproducts in the gas stream; and
- a flow conduit configured to recycle the separated hydrogen to the hydrothermolysis reactor.

\* \* \* \* \*